United States Patent [19]

Amou et al.

[11] Patent Number: 5,451,346
[45] Date of Patent: Sep. 19, 1995

[54] FRAGRANT PERACETIC ACID-CONTAINING OXIDIZING COMPOSITION

[75] Inventors: Tadashi Amou, Tokyo; Tohru Nakasugi; Atsushi Takahashi, both of Osaka; Osamu Machida, Kohriyama; Toshio Yasunaga, Tokyo; Katsuko Hiraguri, Kohriyama, all of Japan

[73] Assignees: Inabata Koryo Co., Ltd., Osaka; Nippon Peroxide Co., Ltd., Tokyo, both of Japan

[21] Appl. No.: 146,396

[22] Filed: Nov. 1, 1993

[30] Foreign Application Priority Data

Nov. 4, 1992 [JP] Japan .................. 4-317937

[51] Int. Cl.⁶ .................. C01B 15/01; C01B 15/10; C11D 3/395; C11D 9/44
[52] U.S. Cl. .................. 252/186.23; 252/186.22; 252/186.26; 252/186.28; 252/95; 252/174.11
[58] Field of Search .............. 252/186.23, 186.22, 252/186.21, 186.26, 186.28, 186.29, 95, 174.11

[56] References Cited

U.S. PATENT DOCUMENTS

| 4,917,815 | 4/1990 | Beilfuss et al. | 252/186.23 |
| 5,368,867 | 11/1994 | Da Silva et al. | 424/616 |

FOREIGN PATENT DOCUMENTS

| 0127557 | 12/1984 | European Pat. Off. . |
| 0193416 | 9/1986 | European Pat. Off. . |
| 0370850 | 5/1990 | European Pat. Off. . |
| 292477 | 8/1991 | Germany . |
| 4-30783 | 5/1990 | Japan . |
| 2-193905 | 7/1990 | Japan . |
| 3-130498 | 6/1991 | Japan . |
| 3-133728 | 6/1991 | Japan . |
| WO93/02973 | 2/1993 | WIPO . |

OTHER PUBLICATIONS

Chemical Patents Index, Documentation Abstract Journal, Sec.Ch, week 8931, Derwent Publications Ltd., London, GB class C, An 225734 [JP-A 1 163 905 (A. Mizunoua) 27 Jun. 1989].

Chemical Patents Index, Basic Abstract Journal, Sec.Ch, week 8707, Derwent Publications Ltd., London, GB class C, An 046867 [JP-A 62-004792 (Kao Corp) 10 Jan. 1987].

*Primary Examiner*—Richard D. Lovering
*Assistant Examiner*—Joseph D. Anthony
*Attorney, Agent, or Firm*—McAulay Fisher Nissen Goldberg & Kiel

[57] ABSTRACT

An oxidizing composition comprises an aqueous solution of peracetic acid, hydrogen peroxide and acetic acid and a fragrant component uniformly solubilized in the peracetic acid-containing aqueous solution by aid of a surfactant component, the fragrant component comprising at least one fragrance material which is chemically stable in the presence of peroxide compounds and effectively masks the irritating odor of peracetic acid and acetic acid.

10 Claims, No Drawings

FRAGRANT PERACETIC ACID-CONTAINING OXIDIZING COMPOSITION

BACKGROUND OF THE INVENTION

1. Field of the Invention

The present invention relates to a fragrant peracetic acid-containing oxidizing composition. More particularly, the present invention relates to a fragrant peracetic acid-containing oxidizing composition in which an oxidizing component comprising peracetic acid, hydrogen peroxide and acetic acid dissolved in water, is mixed with a chemically and physically stable fragrance material, and the irritating odor of the oxidizing component is masked by the fragrance material.

2. Description of the Related Art

It is known that an aqueous solution containing peracetic acid, hydrogen peroxide and acetic acid, which will be referred to as a peracetic acid-containing aqueous solution hereinafter, exhibits a high bactericidal activity and an excellent biodegradability at a relatively low temperature and thus is useful as a bactericide for asptic package (JP-A-3-130,498), a bactericidal material for a food container (JP-A-3-133,728 and JP-A-4-30,783) and a hygienic material for blood dialysis (JP-A-2-193,905). Also, the peracetic acid-containing aqueous solution is widely utilized as an excellent disinfectant and bactericide which do not damage materials of equipments, machines and apparatuses, for example, storage tanks, brewing apparatuses, pipe lines and other attachments in food factories which are required to have a high level of hygienic technique and safety.

The peracetic acid-containing aqueous solution is, however, disadvantages in that it has a specific irritating odor of peracetic acid and acetic acid, and this irritating odor is difficult to remove. This odor will be referred to as an irritating peracetic acid odor hereinafter. Therefore, the peracetic acid-containing aqueous solution is now used only in limited fields, for example, the food industry, and for specific purposes.

With respect to chlorine-containing bleaching agents which are widely used as a disinfectant and bleaching agents for household uses, it is pointed out that chlorine exhibits a high toxicity. Thus, an oxygen type disinfectant and bleaching agent, namely the peracetic acid-containing aqueous solution, is expected to be utilized for or applied to household uses. However, the irritating peracetic acid odor binders the wide utilization and application of the peracetic acid-containing aqueous solution.

The irritating odor of the peracetic acid-containing aqueous solution is an inherent property derived from peracetic acid and acetic acid. Therefore, it is impossible to make the peracetic acid-containing aqueous solution odorless by chemical and/or physical means without reducing the content of peracetic acid and hydrogen peroxide (which will be referred to as an effective ingredient hereinafter) in the aqueous solution.

SUMMARY OF THE INVENTION

An object of the present invention is to provide a fragrant peracetic acid-containing oxidizing composition free from an irritating odor and thus useful as a home disinfectant and bleaching agent.

Another object of the present invention is to provide a fragrant peracetic acid-containing oxidizing composition enabling a peracetic acid-containing aqueous solution to be widely utilized in expanded uses.

The inventors of the present invention have attempted to mask the irritating odor of the peracetic acid-containing aqueous solution with a fragrance material and thus completed the present invention.

The above-mentioned objects can be attained by the fragrant peracetic acid-containing oxidizing composition of the present invention which comprises (1) an oxidizing component comprising an aqueous solution of peracetic acid, hydrogen peroxide and acetic acid; (2) a fragrant component comprising at least one fragrance material which is chemically stable in the presence of the oxidizing component and capable of masking the irritating odor of the oxidizing component; and (3) a surfactant component for causing the fragrant component to be stably solubilized in the oxidizing component.

To these ends, the present invention consists in the provision of a fragrant peracetic acid-containing an oxidizing composition comprising an oxidizing component comprising an aqueous solution of 0.1 to 10% by weight of peracetic acid, 1 to 10% by weight of hydrogen peroxide and 2 to 40% by weight of acetic acid, based on the total weight of the composition, a fragrant component comprising at least one fragrance material which is chemically stable in the presence of the oxidizing component and capable of masking the irritating odor of the oxidizing component, in a content of 0.01 to 2.0% by weight based on the total weight of the composition, and a surfactant component comprising at lest one non-ionic surfactant compound which causes the fragrant component to be stably solubilized in the oxidizing component, in a content of 0.5 to 5 % by weight based on the total weight of the composition.

DESCRIPTION OF THE PREFERRED EMBODIMENTS

In the fragrant peracetic acid-containing oxidizing composition of the present invention, the oxidizing component comprises an aqueous solution of peracetic acid, hydrogen peroxide and acetic acid. In this oxidizing component, a solution medium comprises at least acetic acid and water.

In the oxidizing component, the content of peracetic acid is preferably 0.1 to 10% by weight, more preferably 0.5 to 6% by weight; the content of hydrogen peroxide is preferably 1 to 10% by weight, more preferably 3 to 6% by weight, and the content of acetic acid is preferably 2 to 40% by weight, more preferably 10 to 30% by weight.

The fragrant component usable for the present invention comprises at least one specific fragrant material selected from synthetic and natural fragrant materials. The specific fragrant material usable for the present invention is required to be capable of masking the irritating odor by the fragrance thereof, without reducing a stability of the effective ingredient in the oxidizing component; chemically stable in the presence of the oxidizing component so that the fragrance-generating property thereof is not reduced by the oxidizing component; and capable of being stably and uniformly solubilized in the appearance of a transparent liquid in the oxidizing component with the aid of the surfactant component.

Usually, the fragrant component comprises a mixture of two or more fragrant material selected in consideration of the inherent fragrance thereof and the abovementioned requirements. Namely, the fragrant component usually comprises a fragrance composition.

In the fragrance peracetic acid-containing oxidizing composition of the present invention, the fragrant component is present preferably in a content of 0.01 to 2.0% by weight, more preferably 0.1 to 1.0% by weight.

The synthetic fragrant compounds, usable for the present invention are classified into hydrocarbons, alcohols, esters, ketones, lactones, acetals, aldehydes and ethers as indicated below.

The synthetic fragrant compounds and the natural fragrant materials include the following compounds and materials.

(A) Hydrocarbons
p-cymene
(B) Alcohols
borneol,
cinnamic alcohol,
dimethyl benzyl carbinol,
l-menthol,
fenchyl alcohol,
phenyl ethyl alcohol,
o-tert-butyl cyclohexanol,
2-sec-butyl cyclohexanol,
lauryl alcohol,
2-methyl undecanol,
hexyl alcohol,
citronellol,
dihydro myrcenol,
iso-amyl alcohol,
tetrahydro linalool,
dipropylene glycol,
hexylene glycol,
p-tert-butyl cyclohexanol,
phenyl hexanol,
3,3,5-trimethyl hexanol,
cis-trimethyl cyclohexanol,
trans-2-hexanol, and
bornyl methoxy cyclohexanol (Santalex)
(C) Esters
ethylene tridecane dioate,
amyl salicylate,
dimethyl benzyl carbinyl acetate,
fenchyl acetate,
n-hexyl salicylate,
iso-bornyl acetate,
o-tert-butyl cyclohexyl acetate,
p-tert-butyl cyclohexyl acetate,
phenyl ethyl acetate,
tricyclodecenyl acetate,
styrallyl acetate,
methyl salicylate,
allylamyl glycolate,
allyl capronate,
ethyl capronate,
ethyl cinnamate,
geranyl acetate,
n-hexyl acetate,
iso-amyl acetate,
iso-nonyl acetate,
triethyl citrate,
rosephenene,
dihydro mycenyl acetate,
butyl-2-methyl varerate, and
trans-2-hexenyl acetate.
(D) Ketones
dl-camphor,
coumarin,
pentyl cyclopentanone,
iso-menthone,
p-hydroxy phenyl butanone,
6-acetyl-1,1,3,4,4,6-hexamethyl tetrahydronaphthalene,
ionone,
p-tert-butyl cyclohexanone,
o-tert-butyl cyclohexanone,
1-(2,6,6-trimethyl-1,3-cyclohexadiene-1-yl)-2-butene-1-one(Damascenone),
1-(2,6,6-trimethyl-2-cyclohexene 1-yl)-2-butene-1-one(Damascone α),
1-(2,6,6-trimethyl-1-cyclohexene-1-yl)-2-butene-1-one(Damascone β),
1-(2,6,6-trimethyl-3-cyclohexene-1-yl)-2-butene-1-one (Delta Damascone),
Dihydro Floriffone TD), and
p-mentha-8-thiol-3-one
(E) Lactones
γ-undecalactone
(F) Acetals
phenyl acetaldehyde dimethylacetal
(G) Aldehydes
octyl aidehyde,
citronellal, and
methyl nonyl acetaldehyde
(H) Ethers
diphenyl oxide,
phenyl ethyl isoamyl ether, and
1,3,4,6,7,8-hexahydro-4,6,6,7,8,8-hexamethyl-cyclopenta-γ-2-benzopyran (Galaxolide)
(I) Natural fragrances
eucalyptus oil,
lavender oil,
lime oil,
pineneedle oil,
peppermint oil,
rosemary oil, and
spearmint oil In the fragrant peracetic acid-containing oxidizing composition of the present invention, the surfactant component is employed to uniformly and stably solubilized the fragrant component as mentioned above in the oxidizing component, namely the peracetic acid-containing aqueous solution, preferably at temperature of from room temperature to 70° C.

In the oxidizing aqueous solution system of the present invention, the surfactant component preferably comprises at least one member selected from non-ionic surface active compounds which are relatively stable in the oxidizing system.

The non-ionic surfactants are preferably selected from:

(a) mixtures of two selected from polyoxyethylene nonyl phenyl ethers having mole numbers of addition-reacted ethylene oxide of 3, 9, 11 and 50, (b) mixtures of one selected from the abovementioned polyoxyethylene nonyl phenyl ethers in (a) with one selected from polyoxyethylene-added hydrogenated castor oils having mole numbers of addition-reacted ethylene oxide of 25, 40 and 80, (c) mixtures of two selected from the polyoxyethylene-added hydrogenated castor oils mentioned in (b), (d) mixtures of one selected from polyoxyethylene lauryl ethers having mole numbers of addition-reacted ethylene oxide of 4 and 23 with a polyoxyethylene stearyl ether having a mole number of addition-reacted ethylene oxide of 12, and (e) mixtures of one selected from polyoxyethylene lauryl ethers as mentioned in (d) with a polyoxyethylene oleyl ether having a mole number of addition-reacted ethylene oxide of 13.

The above-mentioned non-ionic surfactants each have an HLB of 12 to 15.

In the fragrant peracetic acid-containing oxidizing composition of the present invention, the surfactant component is preferably present in a content of 0.5 to 5.0% by weight. The amount of the surfactant component is variable depending on the type and content of the fragrant component. Also, in the present invention, the type of the non-ionic surfactant compound and the composition of the surfactant component should be established so that the fragrant component can be o/w type solubilized in the oxidizing component by aid of the surfactant component, and the resultant oxidizing composition exhibits the same liquid appearance as that of the peracetic acid-containing aqueous solution of the oxidizing component.

Also, it is important that the fragrant component and the surfactant component be chemically stable and not reactive with the oxidizing component, and thus the addition of the fragrant component and the surfactant component does not cause the content of the effective ingredient in the oxidizing component to be reduced.

The fragrant peracetic acid-containing oxidizing composition of the present invention optionally contains an additive, for example, a coloring material or thickener.

EXAMPLES

The present invention will be further explained by the following specific examples.

Examples 1 to 61 and Comparative Examples 1 and 2

In each of Examples 1 to 61, an oxidizing component was prepared by dissolving 1.05% by weight of peracetic acid, 5.55% of hydrogen peroxide and 15% of acetic acid in water. This aqueous solution had a pH of 1.6.

A surfactant component was prepared by mixing 84.6% by weight of a polyoxyethylene oleyl ether having a mole number of addition-reacted ethylene oxide of 13 with 15.4% by weight of a polyoxyethylene lauryl ether having a mole number of addition reacted ethylene oxide of 4. The resultant surfactant component had an HLB of 13.0.

A fragrance component consisted of a fragrance material as indicated in Tables 1 to 4. When the fragrance material is in the state of a crystal or a viscous liquid, it was preliminarily dissolved in a concentration of 20% by weight in dipropylene glycol (DPG).

The fragrant component in an amount of 0.2 parts by weight was uniformly dissolved in 1.0 or 2.0 parts by weight of the surfactant component. To the resultant fragrant component-surfactant component solution, the oxidizing component was added in an amount sufficient to provide an oxidizing composition in a total amount of 100 parts by weight. The mixture was heated at a temperature of 50° C.

A transparent fragrant composition in the state of a solution was obtained.

The resultant fragrant peracetic acid-containing oxidizing composition was subjected to the following tests.

A sample of the resultant composition was placed in an amount of 50 ml in a glass jar having a capacity of 100 ml and the jar was closed with a stopper. The jar was stored in a constant temperature bath at a temperature of −5° C. or 40° C. for 20 days. Then, the jar was taken out from the constant temperature bath and conditioned at room temperature. Then the jar was opened, and the odor of the composition in the jar was smelled at the mouth of the jar and evaluated by a smelling speciality panel in comparison with the odor of the oxidizing component containing no fragrant component, to establish the masking effect of the fragrant composition on the irritating odor of the oxidizing component.

Also, the odor of the composition stored at 40° C. for 20 days was compared with the odor of the fresh composition immediate after the preparation thereof, to evaluate the fragrance stability of the composition.

Further, the appearance of the composition stored at 40° C. for 20 days was compared with that of the fresh composition to evaluate the appearance stability of the composition.

The results of the tests were classified and indicated in the following manner.

Masking effect
4: No irritating odor of peracetic acid and acetic acid was noted and only the fragrance of the fragrant component was noted.
3: The irritating odor was noted very little and the fragrance of the fragrant component was mainly noted.
2: A little irritating odor mixed with the fragrance of the fragrant component was noted.
1: Strong irritating odor was noted.

Fragrance stability
4: Substantially no change in fragrance occurred.
3: Very little change in fragrance occurred.
2: Little change in fragrance occurred. The remaining fragrance was still effective for masking.
1: Clear change in fragrance occurred.

Appearance stability
3: No change in appearance occurred.
2: White turbidity occurred slightly.
1: Precipitation occurred.

Further, the fragrant compositions immediate after the preparation thereof and after storage for 20 days at 40° C. were subjected to measurements of the concentration of peracetic acid and the total concentration of peroxide compounds (effective ingredient) to evaluate the stability of the effective ingredient.

Analysis

A sample of a fragrant composition was accurately weighed and mixed with about 100 ml of pure water. This mixture was added to an aqueous potassium iodide solution in a slightly excessive equivalent amount with respect to the amount of peracetic acid. The amount of iodine liberated from potassium iodide was measured by a titration of a standard aqueous sodium thiosulfate aqueous solution to determine the concentration of peracetic acid. Then, a diluted sulfuric acid an aqueous potassium iodide solution in a greatly excessive amount, and an aqueous ammonium molybdate solution were added to the titrated mixture. The amount of iodine liberated from potassium iodide was measured by a titration of a standard aqueous sodium thiosulfate, to determine the concentration of hydrogen peroxide.

The total concentration of the peroxide compounds (effective ingredient) was calculated from the sum of the concentrations of peracetic acid and hydrogen peroxide and indicated in terms of the concentration of hydrogen peroxide. The test results are shown in Tables 1 to 8.

In Comparative Example 1, the same procedures and tests as in Example 1 were carried out except that the fragrant component and the surfactant component were omitted.

In Comparative Example 2, the same procedures and tests as in Example 1 were carried out except that the fragrant component was omitted.

The test results are shown in Tables 1 and 5.

TABLE 1

| Example No. | | Type of fragrant material | Masking effect | Fragrance stability | Appearance stability −5° C./ 20 days | Appearance stability 40° C./ 20 days |
|---|---|---|---|---|---|---|
| Comparative Example | 1 | Control (oxidizing component) | None | — | — | — |
| | 2 | Control (oxidizing and surfactant components) | None | — | — | — |
| | | [Hydrocarbons] | | | | |
| Example | 1 | p-Cymene | 4 | 4 | 3 | 3 |
| | | [Alcohols] | | | | |
| | 2 | Borneol (20% DPG solution) | 3 | 3 | 3 | 3 |
| | 3 | Cinnamic alcohol | 3 | 3 | 3 | 3 |
| | 4 | Dimethyl benzyl carbinol | 2 | 4 | 3 | 3 |
| | 5 | 1-Menthol (20% DPG solution) | 3 | 3 | 3 | 3 |
| | 6 | Fenchyl alcohol | 4 | 4 | 3 | 3 |
| | 7 | Phenyl ethyl alcohol | 3 | 3 | 3 | 3 |
| | 8 | o-tert-Butylcyclohexanol | 4 | 4 | 3 | 3 |
| | 9 | 2-sec-Butylcyclohexanol | 3 | 3 | 3 | 3 |
| | 10 | Lauryl alcohol | 3 | 4 | 3 | 3 |
| | 11 | 2-Methyl undecanol | 3 | 4 | 3 | 3 |
| | 12 | Hexyl alcohol | 4 | 4 | 3 | 3 |
| | 13 | Citronellol | 3 | 4 | 3 | 3 |
| | 14 | Dihydromyrcenol | 3 | 4 | 3 | 3 |
| | 15 | iso-Amyl alcohol | 4 | 4 | 3 | 3 |
| | 16 | Tetrahydrolinalool | 4 | 4 | 3 | 3 |
| | 17 | Dipropylene glycol | 2 | 4 | 3 | 3 |
| | 18 | Hexylene glycol | 2 | 4 | 3 | 3 |

TABLE 2

| Example No. | Type of fragrant material | Masking effect | Fragrance stability | Appearance stability −5° C./ 20 days | Appearance stability 40° C./ 20 days |
|---|---|---|---|---|---|
| | [Esters] | | | | |
| Example 19 | Ethylenetridecane dioate | 3 | 3 | 3 | 2 |
| 20 | Amyl salicylate | 4 | 3 | 3 | 3 |
| 21 | Dimethyl benzyl carbinyl acetate | 4 | 3 | 3 | 3 |
| 22 | Fenchyl acetate | 4 | 3 | 3 | 3 |
| 23 | n-Hexyl salicylate | 3 | 4 | 3 | 3 |
| 24 | iso-Bornyl acetate | 4 | 4 | 3 | 3 |
| 25 | o-tert-Butylcyclohexyl acetate | 4 | 3 | 3 | 3 |
| 26 | p-tert-Butylcyclohexyl acetate | 4 | 3 | 3 | 3 |
| 27 | Rosephenone | 4 | 4 | 1 | 3 |
| 28 | Phenylethyl acetate | 4 | 3 | 3 | 3 |
| 29 | Tricyclodecenyl acetate | 3 | 3 | 3 | 3 |
| 30 | Styrallyl acetate | 4 | 3 | 3 | 3 |
| 31 | Methyl salicylate | 4 | 4 | 3 | 3 |
| 32 | Allylamyl glycolate | 4 | 3 | 3 | 3 |
| 33 | Allyl capronate | 4 | 3 | 3 | 3 |
| 34 | Ethyl capronate | 4 | 3 | 3 | 3 |
| 35 | Ethyl cinnamate | 3 | 3 | 3 | 3 |
| 36 | Geranyl acetate | 4 | 3 | 3 | 3 |
| 37 | n-Hexyl acetate | 4 | 3 | 3 | 3 |
| 38 | iso-Amyl acetate | 4 | 3 | 3 | 3 |
| 39 | iso-Nonyl acetate | 4 | 4 | 3 | 3 |
| 40 | Triethyl citrate | 2 | 4 | 3 | 3 |

TABLE 3

| Example No. | Type of fragrant material | Masking effect | Fragrance stability | Appearance stability −5° C./ 20 days | Appearance stability 40° C./ 20 days |
|---|---|---|---|---|---|
| | [Ketones] | | | | |

TABLE 3-continued

| Example No. | | Type of fragrant material | Masking effect | Fragrance stability | Appearance stability −5° C./ 20 days | Appearance stability 40° C./ 20 days |
|---|---|---|---|---|---|---|
| Example | 41 | dl-camphor (20% DPG solution) | 4 | 3 | 3 | 3 |
| | 42 | Coumarin (20% DPG solution) | 3 | 4 | 3 | 3 |
| | 43 | Pentyl cyclopentanone | 4 | 4 | 3 | 3 |
| | 44 | iso-Menthone | 4 | 3 | 3 | 3 |
| | 45 | p-Hydroxyphenyl butanone (20% DPG solution) | 4 | 3 | 3 | 3 |
| | 46 | 6-Acetyl-1,1,3,4,4,6-hexamethyltetrahydronaphthalene | 4 | 3 | 1 | 3 |
| | 47 | Ionone | 3 | 3 | 3 | 3 |
| | | [Lactones] | | | | |
| | 48 | γ-Undecalactone | 4 | 3 | 3 | 3 |
| | | [Acetals] | | | | |
| | 49 | Phenylacetaldehydedimethyl acetal | 4 | 4 | 3 | 3 |
| | | [Aldehydes] | | | | |
| | 50 | Octyl aldehyde | 3 | 3 | 3 | 3 |
| | 51 | Methylnonyl acetaldehyde | 4 | 3 | 3 | 2 |
| | 52 | Citronellal | 3 | 3 | 3 | 3 |
| | | [Ethers] | | | | |
| | 53 | Diphenyl oxide | 4 | 3 | 1 | 3 |
| | 54 | Phenylethylisoamyl ether | 4 | 3 | 2 | 3 |

TABLE 4

| Example No. | | Type of fragrant material | Masking effect | Fragrance stability | Appearance stability −5° C./ 20 days | Appearance stability 40° C./ 20 days |
|---|---|---|---|---|---|---|
| | | [Natural fragrant material] | | | | |
| Example | 55 | Eucalyptus oil | 4 | 3 | 3 | 3 |
| | 56 | Lavender oil | 3 | 3 | 3 | 3 |
| | 57 | Lime oil | 4 | 3 | 3 | 3 |
| | 58 | Pineneedle oil | 4 | 4 | 3 | 3 |
| | 59 | Peppermint oil | 4 | 3 | 3 | 3 |
| | 60 | Rosemary oil | 4 | 3 | 3 | 3 |
| | 61 | Spearmint oil | 3 | 3 | 3 | 3 |

TABLE 5

| Example No. | | Type of fragrance material | Content of surfactant component | Immediately after preparation of composition PAA(*)$_1$ content (%) | Immediately after preparation of composition H$_2$O$_2$ content (%) | Immediately after preparation of composition T.P. content(*)$_2$ (%) | After 20 day storage of composition at 40° C. PAA content (%) | After 20 day storage of composition at 40° C. H$_2$O$_2$ content (%) | After 20 day storage of composition at 40° C. T.P. content(*)$_2$ (%) | Stability (*)$_3$ (%) |
|---|---|---|---|---|---|---|---|---|---|---|
| Comparative Example | 1 | Control (oxidizing component) | — | 1.12 | 5.47 | 5.97 | 1.10 | 5.24 | 5.73 | 96.0 |
| | 2 | Control (oxidizing and surfactant components) | 1.0 | 1.07 | 5.40 | 5.88 | 1.12 | 5.15 | 5.65 | 96.1 |
| | | [Hydrocarbons] | | | | | | | | |
| Example | 1 | p-Cymene | 1.0 | 1.08 | 5.40 | 5.88 | 1.12 | 5.19 | 5.69 | 96.8 |
| | | [Alcohols] | | | | | | | | |
| | 2 | Borneol (20% DPG solution) | 1.0 | 1.07 | 5.42 | 5.90 | 1.07 | 5.13 | 5.61 | 95.1 |
| | 3 | Cinnamic alcohol | 1.0 | 0.98 | 5.19 | 5.62 | 1.08 | 5.12 | 5.60 | 94.9 |
| | 4 | Dimethyl benzyl carbinol | 1.0 | 1.06 | 5.42 | 5.89 | 1.12 | 5.24 | 5.74 | 97.5 |
| | 5 | λ-Menthol (20% DPG solution) | 1.0 | 1.06 | 5.39 | 5.86 | 1.09 | 5.15 | 5.63 | 96.1 |
| | 6 | Fenchyl alcohol | 1.0 | 1.09 | 5.36 | 5.84 | 1.11 | 5.17 | 5.67 | 97.1 |
| | 7 | Phenyl ethyl alcohol | 1.0 | 1.10 | 5.40 | 5.89 | 1.11 | 5.29 | 5.79 | 98.3 |
| | 8 | o-tert-Butylcyclohexanol | 1.0 | 1.09 | 5.43 | 5.92 | 1.09 | 5.14 | 5.62 | 94.9 |
| | 9 | 2-sec-Butylcyclohexanol | 1.0 | 1.03 | 5.35 | 5.81 | 1.12 | 5.13 | 5.63 | 96.9 |
| | 10 | Lauryl alcohol | 2.0 | 1.01 | 5.32 | 5.77 | 1.08 | 5.10 | 5.58 | 96.7 |
| | 11 | 2-Methyl undecanol | 1.0 | 1.06 | 5.33 | 5.80 | 1.04 | 5.05 | 5.51 | 95.0 |
| | 12 | Hexyl alcohol | 1.0 | 1.09 | 5.36 | 5.85 | 1.08 | 5.16 | 5.65 | 96.6 |
| | 13 | Citronellol | 1.0 | 1.02 | 5.33 | 5.78 | 1.04 | 5.09 | 5.56 | 96.2 |
| | 14 | Dihydromyrcenol | 1.0 | 1.02 | 5.36 | 5.82 | 1.11 | 5.07 | 5.56 | 95.5 |
| | 15 | iso-Amyl alcohol | 1.0 | 1.06 | 5.40 | 5.87 | 1.08 | 5.07 | 5.55 | 94.5 |
| | 16 | Tetrahydrolinalool | 1.0 | 1.08 | 5.36 | 5.84 | 1.05 | 5.08 | 5.56 | 95.2 |
| | 17 | Dipropylene glycol | 1.0 | 1.07 | 5.31 | 5.79 | 1.05 | 5.03 | 5.50 | 95.0 |
| | 18 | Hexylene glycol | 1.0 | 1.07 | 5.39 | 5.87 | 1.05 | 5.02 | 5.49 | 93.5 |

Note:
(*)$_1$ ... PAA = Peracetic acid
(*)$_2$ ... T.P. content = Total peroxide content
(*)$_3$ ... Stability ... A ratio of T.P. content immediate after the preparation of composition to T.P. content after 20 day storage of the composition at 40° C.

TABLE 6

| Example No. | | Type of fragrance material | Content of surfactant component | Immediately after preparation of composition | | | After 20 day storage of composition at 40° C. | | | Stability (%) |
|---|---|---|---|---|---|---|---|---|---|---|
| | | | | PAA content (%) | $H_2O_2$ content (%) | T.P. content (%) | PAA content (%) | $H_2O_2$ content (%) | T.P. content (%) | |
| | | [Esters] | | | | | | | | |
| Example | 19 | Ethylenetridecane dioate | 1.0 | 1.13 | 5.36 | 5.86 | 1.12 | 5.23 | 5.73 | 97.8 |
| | 20 | Amyl salicylate | 1.0 | 1.11 | 5.26 | 5.76 | 1.12 | 5.21 | 5.71 | 99.1 |
| | 21 | Dimethyl benzyl carbinyl acetate | 1.0 | 1.10 | 5.37 | 5.86 | 1.10 | 5.22 | 5.71 | 97.4 |
| | 22 | Fenchyl acetate | 1.0 | 1.11 | 5.15 | 5.65 | 1.08 | 5.17 | 5.65 | 100.0 |
| | 23 | n-Hexyl salicylate | 2.0 | 1.03 | 5.29 | 5.75 | 1.07 | 5.13 | 5.61 | 97.6 |
| | 24 | iso-Bornyl acetate | 1.0 | 1.08 | 5.34 | 5.82 | 1.03 | 5.06 | 5.52 | 94.8 |
| | 25 | o-tert-Butylcyclohexyl acetate | 1.0 | 1.12 | 5.31 | 5.82 | 1.11 | 5.28 | 5.77 | 99.1 |
| | 26 | p-tert-Butylcyclohexyl acetate | 1.0 | 1.11 | 5.34 | 5.83 | 1.01 | 4.97 | 5.42 | 93.0 |
| | 27 | Rosephenone | 1.0 | 1.09 | 5.35 | 5.83 | 1.07 | 5.24 | 5.72 | 98.1 |
| | 28 | Phenylethyl acetate | 1.0 | 1.10 | 5.35 | 5.84 | 1.12 | 5.21 | 5.70 | 97.6 |
| | 29 | Tricyclodecenyl acetate | 1.0 | 1.06 | 5.30 | 5.77 | 1.07 | 5.21 | 5.69 | 98.6 |
| | 30 | Styrallyl acetate | 1.0 | 1.05 | 5.31 | 5.78 | 1.06 | 5.10 | 5.57 | 96.4 |
| | 31 | Methyl salicylate | 1.0 | 1.10 | 5.36 | 5.85 | 1.06 | 5.20 | 5.68 | 97.1 |
| | 32 | Allylamyl glycolate | 1.0 | 1.08 | 5.28 | 5.76 | 1.03 | 4.98 | 5.44 | 94.4 |
| | 33 | Allyl capronate | 1.0 | 1.08 | 5.33 | 5.81 | 1.04 | 5.04 | 5.51 | 94.8 |
| | 34 | Ethyl capronate | 1.0 | 1.11 | 5.34 | 5.84 | 1.07 | 5.15 | 5.63 | 96.4 |
| | 35 | Ethyl cinnamate | 1.0 | 1.09 | 5.28 | 5.76 | 1.08 | 5.19 | 5.67 | 98.4 |
| | 36 | Geranyl acetate | 1.0 | 1.10 | 5.37 | 5.86 | 1.10 | 5.01 | 5.50 | 93.9 |
| | 37 | n-Hexyl acetate | 1.0 | 1.11 | 5.36 | 5.86 | 1.04 | 5.06 | 5.53 | 94.4 |
| | 38 | iso-Amyl acetate | 1.0 | 1.08 | 5.27 | 5.75 | 1.03 | 5.03 | 5.49 | 95.5 |
| | 39 | iso-Nonyl acetate | 1.0 | 1.07 | 5.36 | 5.84 | 1.04 | 5.15 | 5.61 | 96.1 |
| | 40 | Triethyl citrate | 1.0 | 1.10 | 5.37 | 5.86 | 1.04 | 5.05 | 5.51 | 94.0 |

TABLE 7

| Example No. | | Type of fragrance material | Content of surfactant component | Immediately after preparation of composition | | | After 20 day storage of composition at 40° C. | | | Stability (%) |
|---|---|---|---|---|---|---|---|---|---|---|
| | | | | PAA content (%) | $H_2O_2$ content (%) | T.P. content (%) | PAA content (%) | $H_2O_2$ content (%) | T.P. content (%) | |
| | | [Ketones] | | | | | | | | |
| Example | 41 | dl-camphor (20% DPG solution) | 1.0 | 1.11 | 5.36 | 5.86 | 1.14 | 5.14 | 5.65 | 96.4 |
| | 42 | Coumarin (20% DPG solution) | 1.0 | 1.10 | 5.37 | 5.86 | 1.09 | 5.24 | 5.72 | 97.6 |
| | 43 | Pentyl cyclopentanone | 1.0 | 1.04 | 5.37 | 5.83 | 1.02 | 5.08 | 5.54 | 95.0 |
| | 44 | iso-Menthone | 1.0 | 1.07 | 5.35 | 5.83 | 1.02 | 5.12 | 5.57 | 95.5 |
| | 45 | p-Hydroxyphenyl butanone (20% DPG solution) | 1.0 | 1.08 | 5.31 | 5.79 | 1.08 | 5.18 | 5.66 | 97.8 |
| | 46 | 6-Acetyl-1,1,3,4,4,6-hexamethyl-tetrahydronaphthalene | 1.0 | 1.09 | 5.35 | 5.83 | 1.07 | 5.25 | 5.72 | 98.1 |
| | 47 | Ionone | 1.0 | 1.00 | 5.34 | 5.79 | 1.05 | 4.98 | 5.45 | 94.1 |
| | | [Lactones] | | | | | | | | |
| | 48 | γ-Undecalactone | 1.0 | 1.12 | 5.39 | 5.89 | 1.04 | 5.10 | 5.56 | 94.4 |
| | | [Acetals] | | | | | | | | |
| | 49 | Phenylacetaldehydedimethyl acetal | 1.0 | 1.08 | 5.34 | 5.82 | 1.08 | 5.17 | 5.66 | 97.3 |
| | | [Aldehyde] | | | | | | | | |
| | 50 | Octyl aldehyde | 1.0 | 1.06 | 5.28 | 5.75 | 1.06 | 5.19 | 5.66 | 98.4 |
| | 51 | Methylnonylacetaldehyde | 1.0 | 1.07 | 5.31 | 5.78 | 1.07 | 5.19 | 5.66 | 97.9 |
| | 52 | Citronellal | 1.0 | 1.05 | 5.33 | 5.80 | 1.06 | 5.12 | 5.59 | 96.4 |
| | | [Ethers] | | | | | | | | |
| | 53 | Diphenyl oxide | 1.0 | 1.12 | 5.34 | 5.84 | 1.08 | 5.30 | 5.78 | 99.0 |
| | 54 | Phenylethylisoamyl ether | 1.0 | 1.17 | 5.36 | 5.89 | 1.06 | 5.20 | 5.67 | 96.3 |

TABLE 8

| Example No. | | Type of fragrance material | Content of surfactant component | Immediately after preparation of composition | | | After 20 day storage of composition at 40° C. | | | Stability (%) |
|---|---|---|---|---|---|---|---|---|---|---|
| | | | | PAA content (%) | $H_2O_2$ content (%) | T.P. content (%) | PAA content (%) | $H_2O_2$ content (%) | T.P. content (%) | |
| | | [Natural fragrant material] | | | | | | | | |
| Example | 55 | Eucalyptus oil | 1.0 | 1.06 | 5.40 | 5.88 | 1.05 | 5.05 | 5.52 | 93.9 |
| | 56 | Lavender oil | 1.0 | 0.99 | 5.40 | 5.84 | 1.02 | 4.98 | 5.44 | 93.2 |
| | 57 | Lime oil | 1.0 | 0.95 | 5.38 | 5.80 | 1.04 | 5.01 | 5.47 | 94.3 |

TABLE 8-continued

|  |  |  | Immediately after preparation of composition | | | After 20 day storage of composition at 40° C. | | | |
| --- | --- | --- | --- | --- | --- | --- | --- | --- | --- |
| Example No. | Type of fragrance material | Content of surfactant component | PAA content (%) | H₂O₂ content (%) | T.P. content (%) | PAA content (%) | H₂O₂ content (%) | T.P. content (%) | Stability (%) |
| 58 | Pineneedle oil | 1.0 | 1.00 | 5.33 | 5.78 | 1.09 | 5.04 | 5.53 | 95.7 |
| 59 | Peppermint oil | 1.0 | 1.03 | 5.34 | 5.80 | 1.04 | 4.99 | 5.46 | 94.1 |
| 60 | Rosemary oil | 1.0 | 1.03 | 5.35 | 5.81 | 1.04 | 4.99 | 5.46 | 94.0 |
| 61 | Spearmint oil | 2.0 | 0.86 | 5.31 | 5.69 | 1.02 | 4.93 | 5.39 | 94.7 |

Tables 1 to 8 clearly show that the fragrant component added to the oxidizing component in the presence of the surfactant component in accordance with the present invention exhibited a high masking effect on the irritating odor of the oxiding component, and the resultant oxidizing composition exhibited a high stability in fragrance thereof and almost of all the oxidizing compositions exhibited a satisfactory stability in appearance thereof.

Almost of all the oxidizing compositions exhibited a stability in total content of the peroxide compounds (effective ingredient) of at least about 93%.

The oxidizing composition of Comparative Example 1 consisting of the oxidizing component alone exhibited a strong irritating odor. Also, the oxidizing composition of Comparative Example 2 consisting of the oxidizing component mixed with the surfactant component exhibited a strong irritating odor.

Some of the fragrance materials used caused a precipitation of crystals or muddying of the composition to occur when stored at a low temperature. These fragrance materials are usable as an ingredient of a fragrance composition.

Example 62

The same procedures as in Example 1 were carried out except that the fragrant oxidizing composition was prepared in the following composition.

| Component | % by weight |
| --- | --- |
| Oxidizing component containing 1.0% by weight of peracetic acid, 5.6% by weight of hydrogen peroxide and 15% by weight of acetic acid | 98.7 |
| Fragrant component | 0.3 |
| Polyoxyethylene lauryl ether (EO mole number = 4) | 0.2 |
| Polyoxyethylene oleyl ether (EO mole number = 13) | 0.8 |

The fragrant component exhibited a floral fragrance and had the following composition.

| Ingredient | % by weight |
| --- | --- |
| n-Hexyl salicylate | 10 |
| iso-Amyl salicylate | 5 |
| Phenylacetaldehyde dimethyl acetal | 20 |
| Cinnamic alcohol | 25 |
| Styrallyl acetate | 5 |
| Phenyl ethyl alcohol | 30 |
| Triethyl citrate | 5 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

Example 63

The same procedures as in Example 1 were carried out except that the fragrant oxidizing composition was prepared in the following composition.

| Component | % by weight |
| --- | --- |
| Oxidizing component containing 1.0% by weight of peracetic acid, 5.6% by weight of hydrogen peroxide and 15% by weight of acetic acid | 97.3 |
| Fragrant component | 0.3 |
| Polyoxyethylene hydrogenated castor oil (EO mole number = 80) | 0.4 |
| Polyoxyethylene hydrogenated castor oil (EO mole number = 40) | 1.6 |

The fragrant component exhibited a floral fragrance and had the following composition.

| Ingredient | % by weight |
| --- | --- |
| Citronellol | 30 |
| Phenylethyl acetate | 10 |
| Phenylethyl alcohol | 40 |
| Geranyl acetate | 5 |
| iso-Nonyl acetate | 5 |
| Ethyl cinnamate | 1 |
| Rosephenone | 2 |
| Diphenyl oxide | 2 |
| Dipropylene glycol | 5 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

Example 64

The same procedures as in Example 1 were carried out except that the fragrant oxidizing composition was prepared in the following composition.

| Component | % by weight |
| --- | --- |
| Oxidizing component containing 1.0% by weight of peracetic acid, 5.6% by weight of hydrogen peroxide and 15% by weight of acetic acid | 97.5 |
| Fragrant component | 0.5 |
| Polyoxyethylene lauryl ether (EO mole number = 4) | 0.4 |
| Polyoxyethylene oleyl ether (EO mole number = 13) | 1.6 |

The fragrant component exhibited a pine herb-like fragrance and had the following composition.

| Ingredient | % by weight |
| --- | --- |
| Pineneedle oil | 25 |
| dl-camphor | 10 |
| Eucalyptus oil | 10 |
| Fenchyl alcohol | 5 |
| iso-Bonyl acetate | 15 |
| Borneol | 5 |
| Lavender oil | 10 |
| Rosemary oil | 8 |
| Methylnonyl acetaldehyde | 2 |
| Dihydromyrcenol | 10 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

Example 65

The same procedures as in Example 64 were carried out except that the fragrant component exhibited a green-like fragrance and had the following composition.

| Ingredient | % by weight |
| --- | --- |
| o-tert-Butylcyclohexyl acetate | 20 |
| o-tert-Butylcyclohexanol | 10 |
| Tetrahydrolinalool | 10 |
| n-Hexyl salicylate | 15 |
| Styrallyl acetate | 10 |
| Allylamyl glycolate | 3 |
| Dihydromyrcenol | 25 |
| Hexyl alcohol | 5 |
| Phenylethylisoamyl ether | 2 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

Example 66

The same procedures as in Example 64 were carried out except that the fragrant component exhibited a fruity fragrance and had the following composition.

| Ingredient | % by weight |
| --- | --- |
| o-tert-Butylcyclohexyl acetate | 40 |
| Ethylene tridecane dioate | 15 |
| γ-Undecalactone | 10 |
| Allyl capronate | 5 |
| n-Hexyl acetate | 5 |
| iso-Amyl acetate | 10 |
| Hexyl alcohol | 5 |
| Allylamyl glycolate | 5 |
| Tricyclodecenyl acetate | 5 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

Example 67

The same procedures as in Example 1 were carried out except that the fragrant oxidizing composition was prepared in the following composition.

| Component | % by weight |
| --- | --- |
| Oxidizing component containing 1.0% by weight of peracetic acid, 5.6% by weight of hydrogen peroxide and 15% by weight of acetic acid | 97.5 |
| Fragrant component | 0.5 |
| Polyoxyethylene lauryl ether (EO mole number = 4) | 0.4 |
| Polyoxyethylene oleyl ether (EO mole number = 13) | 1.6 |

The fragrant component exhibited a woody fragrance and had the following composition.

| Ingredient | % by weight |
| --- | --- |
| Coumarin | 10 |
| Dibenzyl carbinyl acetate | 5 |
| p-tert-Butylcyclohexyl acetate | 50 |
| Ionone | 15 |
| iso-Bornyl acetate | 10 |
| 6-Acetyl-1,1,3,4,4-6-hexamethyl-tetrahydronaphtalene | 10 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

Example 68

The same procedures as in Example 7 were carried out except that the fragrant component exhibited a citrus fragrance and had the following composition.

| Ingredient | % by weight |
| --- | --- |
| Lime oil | 45 |
| Fenchyl alcohol | 30 |
| Citronellal | 5 |
| p-Cymene | 10 |
| Octyl aldehyde | 5 |
| Hexylene glycol | 5 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

As explained above, a stable fragrant peracetic acid-containing oxidizing composition, in which the irritating odor due to the peracetic acid and acetic acid is effectively masked by the fragrant component, could be obtained in accordance with the present invention.

The fragrant oxidizing composition of the present invention exhibits a high bactericidal activity and an excellent biodegradability at a relatively low temperature. Also, the irritating odor of the peracetic acid and acetic acid could be effectively masked by the fragrant component. Further, the oxidizing compounds and the fragrant component in the composition exhibit a satisfactory stability for practical use.

Accordingly, the fragrant oxidizing composition of the present invention can be comfortably employed as a disinfectant, bactericide, bleaching agent, fungicide and deodorizer not only in industries but also at home.

Example 69

The same procedures as in Example 1 were carried out except that the fragrant oxidizing composition was prepared in the following composition.

| Component | % by weight |
| --- | --- |
| Oxidizing component containing 1.0% by weight of peracetic acid, 5.5% by weight of hydrogen peroxide and 15% by weight of acetic acid | 98.7 |
| Fragrant component | 0.3 |
| Polyoxyethylene lauryl ether (EO mole number = 4) | 0.2 |
| Polyoxyethylene oleyl ether (EO mole number = 13) | 0.8 |

The fragrant component exhibited a woody fragrance and had the following composition.

| Ingredient | % by weight |
| --- | --- |
| Cyclodecyl alcohol | 10.0 |
| p-tert-Butyl cyclohexanone | 20.0 |
| 3,3,5-Trimethyl hexanole | 20.0 |
| Bornyl methoxy cyclohexanol | 5.0 |
| 1,3,4,6,7,8-hexahydro-4,6,6,7,8,8-hexamethyl-cyclopenta-γ-2-benzopyran | 15.0 |
| p-tert-Butylcyclohexyl acetate | 30.0 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

Example 70

The same procedures as in Example 79 were carried out with the following exception.

The fragrant component exhibited a rosy floral fragrance and had the following composition.

| Ingredient | % by weight |
| --- | --- |
| Citronellol | 10.0 |
| Phenyl hexanol | 20.0 |
| iso-Nonyl acetate | 10.0 |
| Rosephenone | 5.0 |
| Phenyl ethyl alcohol | 50.0 |
| 1-(2,6,6-Trimethyl-1,3-cyclohexadiene-1-yl)-2-butene-1-one | 5.0 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

Example 71

The same procedures as in Example 69 were carried out with the following exception.

The fragrant component exhibited a green fruity fragrance and had the following composition.

| Ingredient | % by weight |
| --- | --- |
| n-Hexyl alcohol | 10.0 |
| tert-2-Hexanol | 10.0 |
| Dihydro myrcenol | 20.0 |
| Dihydro myrcenyl acetate | 10.0 |
| o-tert-Butyl cyclohexyl acetate | 25.0 |
| Tetrahydro myrcenol | 10.0 |
| Tetrahydro linalool | 10.0 |
| γ-Undecalactone | 5.0 |

It was confirmed that the irritating odor of the oxidizing component was satisfactorily masked and when stored at a temperature of 40° C. or −5° C. for 20 days, the composition exhibited satisfactory stabilities in fragrance, appearance and content of peroxide compounds.

We claim:

1. A fragrant peracetic acid-containing an oxidizing composition comprising:

(1) an oxidizing component comprising an aqueous solution of 0.1 to 10% by weight of peracetic acid, 1 to 10% by weight of hydrogen peroxide and 2 to 40% by weight of acetic acid, based on the total weight of the composition;

(2) a fragrant component comprising at least one fragrance material which is chemically stable in the presence of the oxidizing component and capable of masking the irritating odor of the oxidizing component, in a content of 0.01 to 2.0% by weight based on the total weight of the composition; and (3) a surfactant component comprising at lest one non-ionic surfactant compound which causes the fragrant component to be stably solubilized in the oxidizing component, in a content of 0.5 to 5% by weight based on the total weight of the composition.

2. The fragrant peracetic acid-containing oxidizing composition as claimed in claim 1, wherein the fragrance material is selected from the group consisting of p-cymene, borneol, cinnamic alcohol, dimethyl benzyl carbinol, l-menthol, fenchyl alcohol, phenyl ethyl alcohol, o-tert-butyl cyclohexanol, 2-sec-butyl cyclohexanol, lauryl alcohol, 2-methyl undecanol, hexyl alcohol, citronellol, dihydro myrcenol, iso-amyl alcohol, tetrahydro linalool, dipropylene glycol, hexylene glycol, ethylene tridecandioate, amyl salicylate, dimethyl benzyl carbinyl acetate, fenchyl acetate, n-hexyl salicylate, iso-bornyl acetate, o-tert-butyl cyclohexyl acetate, p-tert butyl cyclohexyl acetate, rosephenone, phenyl ethyl acetate, tricyclodecenyl acetate, styrallyl acetate, methyl salicylate, allylamyl glycolate, allyl capronate, ethyl capronate, ethyl cinnamate, geranyl acetate, n-hexyl acetate, iso-amyl acetate, iso-nonyl acetate, triethyl citrate, dl-camphor, coumarin, pentyl cyclopentanone, iso-menthone, p-hydroxy phenyl butanone, 6-acetyl-1,1,3,4,4,6-hexamethyl tetrahydro naphthalene, ionone, γ-undecalactone, phenyl acetaldehyde dimethyl acetal, octyl aidehyde, citronellal, methylnonyl acetaldehyde, diphenyl oxide, phenylethyl iso-amyl ether, eucalyptus oil, lavender oil, lime oil, pineneedle oil, peppermint oil, rosemary oil, spearmint oil, and p-tert-butyl cyclohexanol, p-tert-butyl cyclohexanone, o-tert-butyl cyclohexanone, 1-(2,6,6-trimethyl-1,3-cyclohexadiene-1-yl)-2-butene-1-one, 1-(2,6,6-trimethyl-2-cyclohexene-1-yl)-2-butene-1-one, 1-(2,6,6-trimethyl-1-cyclohexene-1-yl)-2-butene-1-one, 1-(2,6,6-trimethyl-3-cyclohexene-1-yl)-2-butene-1-one, phenyl hexanol, 3,3,5-trimethyl hexanol, cis-trimethyl cyclohexanol, dihydro myrcenyl acetate, p-mentha-8-thiol-3-one, ethyl-2-methyl valerate, tert-2-hexanol, tert-2-hexenyl acetate, 1,3,4,6,7,8-hexahydro-4,6,6,7,8,8-hexamethyl-cyclopenta-γ-2benzopyran, and bornyl methoxy cyclohexanol.

3. The fragrant peracetic acid-containing oxidizing composition as claimed in claim 1, wherein the surfactant component exhibits an HLB of 12 to 15.

4. The flagrant peracetic acid oxidizing composition as claimed in claim 1, wherein the hydrogen peroxide content is between 3 to 6% by weight.

5. The fragrant peracetic acid oxidizing composition as claimed in claim 1, wherein the fragrant component is 0.1 to 1.0% by weight.

6. The flagrant peracetic acid oxidizing composition as claimed in claim 5, wherein the hydrogen peroxide content is between 3 to 6% by weight.

7. The fragrant peracetic acid oxidizing composition as claimed in claim 1, wherein the content of the peracetic acid is 0.5 to 6% by weight and the content of the acetic acid is preferably 10 to 30% by weight.

8. The flagrant peracetic acid oxidizing composition as claimed in claim 7, wherein the hydrogen peroxide content is between 3 to 6% by weight.

9. The flagrant peracetic acid oxidizing composition as claimed in claim 7, wherein the flagrant component is 0.1 to 1.0% by weight.

10. The fragrant peracetic acid oxidizing composition as claimed in claim 9, wherein the hydrogen peroxide content is between 3 to 6% by weight.

* * * * *